(12) United States Patent
Abernathie

(10) Patent No.: US 7,780,732 B2
(45) Date of Patent: Aug. 24, 2010

(54) SPINAL FUSION CAGE AND METHOD OF USE

(76) Inventor: Dennis Lee Abernathie, 5320 S. State Hwy. 163, Columbia, MO (US) 65203

( * ) Notice: Subject to any disclaimer, the term of this patent is extended or adjusted under 35 U.S.C. 154(b) by 0 days.

(21) Appl. No.: 11/081,162

(22) Filed: Mar. 16, 2005

(65) Prior Publication Data
US 2006/0212118 A1 Sep. 21, 2006

(51) Int. Cl.
A61F 2/44 (2006.01)
(52) U.S. Cl. ................................. 623/17.11
(58) Field of Classification Search ............. 623/17.11, 623/17.12, 17.15, 17.16; 606/61
See application file for complete search history.

(56) References Cited
U.S. PATENT DOCUMENTS 6,113,638 A * 9/2000 Williams et al. ............. 128/898
6,176,882 B1 * 1/2001 Biedermann et al. ...... 623/17.15
6,217,579 B1 * 4/2001 Koros .......................... 606/61
6,562,074 B2 * 5/2003 Gerbec et al. ............. 623/17.15
6,641,614 B1 * 11/2003 Wagner et al. ............ 623/17.15
2002/0029084 A1 * 3/2002 Paul et al. ................. 623/23.63
2004/0030387 A1 * 2/2004 Landry et al. ............. 623/16.11
2005/0060034 A1 * 3/2005 Berry et al. ............... 623/17.11
2005/0154459 A1 * 7/2005 Wolek et al. .............. 623/17.11
2006/0195191 A1 * 8/2006 Sweeney et al. .......... 623/17.13

* cited by examiner

Primary Examiner—Thomas C Barrett
Assistant Examiner—Nicholas Woodall

(57) ABSTRACT

The present invention provides a fusion cage comprising a first housing, a second housing, and an alignment portion adapted to be received between the first and second housings such that the first and second housings are held in place by said alignment portion. The alignment portion can be varied in shape such that the fusion cage is wedge-like in shaped, or slanted to one side. Further, the alignment portion is constructed of a radiolucent material to allow for visualization of a bone fusion within the fusion cage.

5 Claims, 10 Drawing Sheets

SPINAL FUSION CAGE AND METHOD OF USE

BACKGROUND OF THE INVENTION

The present invention relates generally to an implantable device for promoting the fusion of adjacent bony structures, and a method of using the same. More specifically, the present invention relates to an expandable fusion cage that may be inserted into an intervertebral space, and a method of using the same.

Fusion cages provide a space for inserting a bone graft between adjacent portions of bone. Such cages are often made of titanium and are hollow, threaded, and porous in order to allow a bone graft contained within the interior of the cage to grow through the cage into adjacent vertebral bodies. Such cages are used to treat a variety of spinal disorders, including degenerative disc diseases such as Grade I or II spondylolistheses of the lumbar spine.

The majority of spinal fusion cages are placed in front of the spine, a procedure known as anterior lumbar interbody fusion, or ALIF. The cages are generally inserted through a traditional open operation, though laparoscopic or percutaneous insertion techniques may also be used. Cages may also be placed through a posterior lumbar interbody fusion, or PLIF, technique, involving placement of the cage through a midline incision in the back.

Regardless of the approach, the typical procedure for inserting a common threaded and impacted fusion cage is the same. First, the disc space between two vertebrae of the lumbar spine is opened using a wedge or other device on a first side of the vertebrae. The disk space is then prepared to receive a fusion cage. Conventionally, a threaded cage is inserted into the bore and the wedge is removed. A disk space at the first side of the vertebrae is then prepared, and a second threaded fusion cage inserted into the bore. Alternatively, the disk space between adjacent vertebrae may simply be cleared and a cage inserted therein. Often, only one cage is inserted obliquely into the disk space. Use of a threaded cage may be foregone in favor of a rectangular or pellet-shaped cage that is simply inserted into the disk space.

Although ALIF is common, the procedure suffers from disadvantages. In cases where patients have a "tall" disc, or where there is instability (such as with isthmic spondylolistheses), an anterior approach to the spinal fusion may not provide adequate stability. Further, the procedure is performed in close proximity to the large blood vessels that go to the legs, thereby risking damage to these blood vessels, which can result in excessive blood loss. In dealing with male patients, another unique risk arises. Approaching the L5-S1 disc space from the front risks a condition known as retrograde ejaculation. This is due to the position of small nerves directly over the disc interspace that control a valve causing the ejaculate to the expelled during intercourse. Dissecting over the disk space can cause the nerves to stop working and, absent innervation to the valve, the ejaculate may move into the bladder.

A problem common to many fusion cages, regardless of method of insertion, concerns maintaining or restoring the normal anatomy of the fused spinal segment. Once a disc or a portion thereof is removed, the normal lordotic or kyphotic curvature of the spine is eliminated. Traditional fusion cages neglect the need to correct this curvature. Such cages may lead to a kyphotic deformity as the vertebrae settles around the implant. Often, revision surgeries are necessary to correct spinal imbalances. Fusion cages have been designed having a wedge-like shape in order to address these issues, but because of the shape of the cage, such devices must heretofore have been implanted using an ALIF procedure, thereby suffering from all of the disadvantages of using that procedure.

A problem with existing titanium cages is that it is difficult to assess spinal fusions postoperatively because the metal of the cage interferes with attempts to evaluate the fusion by x-ray. Radiolucent cages, such as those made from either carbon fiber or polyetheretherketone (PEEK), have been used to provide better postoperative visualization of spinal fusions. A problem with such cages, however, is that they do not adhere well to the bony endplates and thus often must be supplemented with pedicle screws.

What is needed, therefore, is a spinal fusion cage suitable for a PLIF procedure that allows for preservation or restoration of the proper lordotic or kyphotic curvature of the spine, provides adequate strength and stability to be used with or without supplements such as pedicle screws, and that can be visualized postoperatively via radiologic procedures such as x-rays and the like.

BRIEF SUMMARY OF THE INVENTION

In a preferred embodiment, the present invention provides a fusion cage comprising a first housing, a second housing, and an alignment portion adapted to be received between the first and second housings such that the first and second housings are held in place by said alignment portion. The housing portions can be varied in shape such that the fusion cage is wedge-like in shape, or slanted to one side. The alignment portion is preferably constructed of a radiolucent material to allow for visualization of a bone fusion within the fusion cage.

In one alternative embodiment of the present invention, the fusion cage includes two separate sidewall portions, the sidewall portions mating to the housing portions of the cage via a male/female channel and flange interaction.

In another embodiment, the present device includes two guide portions that serve to place the housing portions of the present device between adjacent vertebrae. The guide portions preferably include rails that the alignment portion may move along in order to be properly inserted between the housing portions.

DETAILED DESCRIPTION OF THE INVENTION

Figure 1:
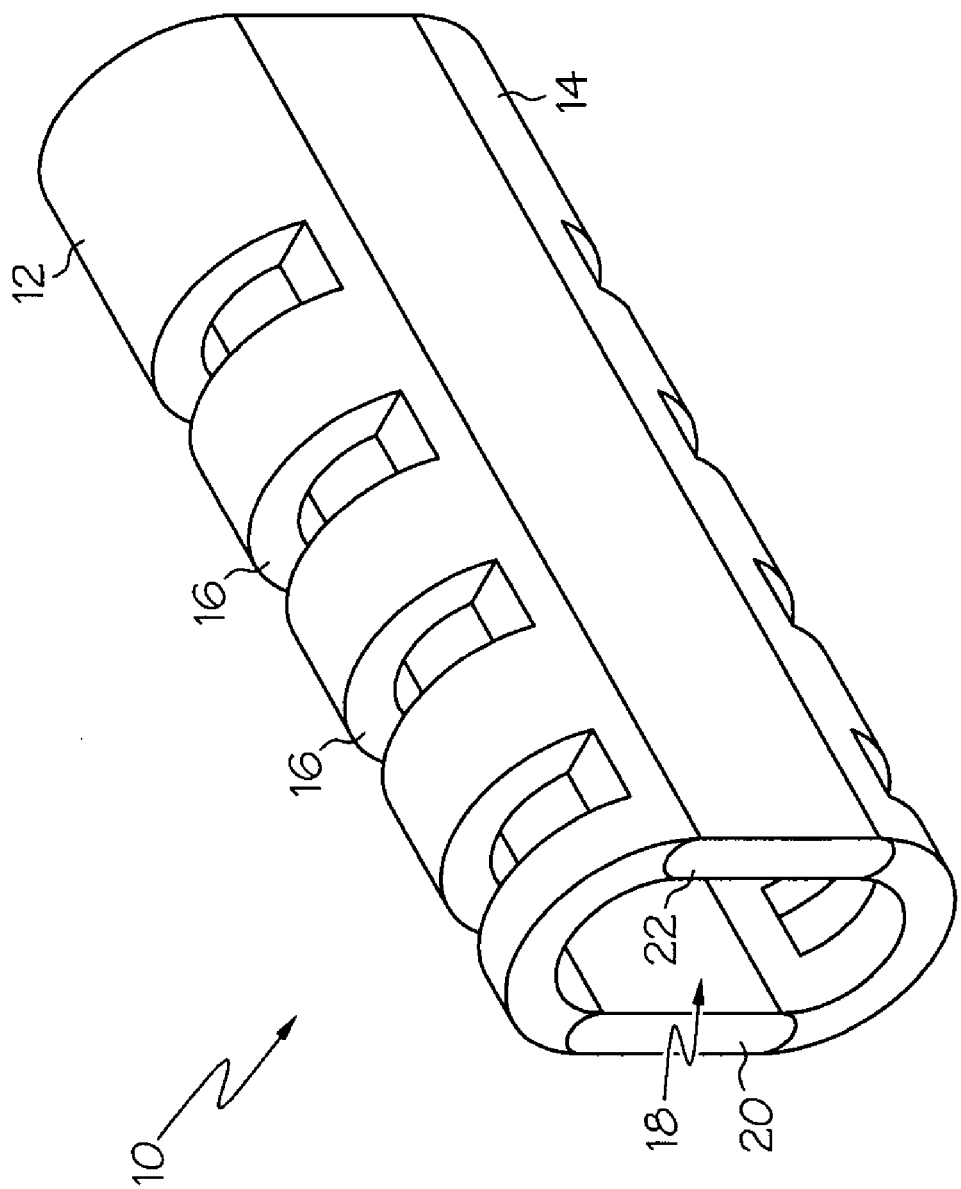
FIG. 1 is a perspective view of a fusion cage constructed in accordance with the teachings of the present invention.
Figure 2:
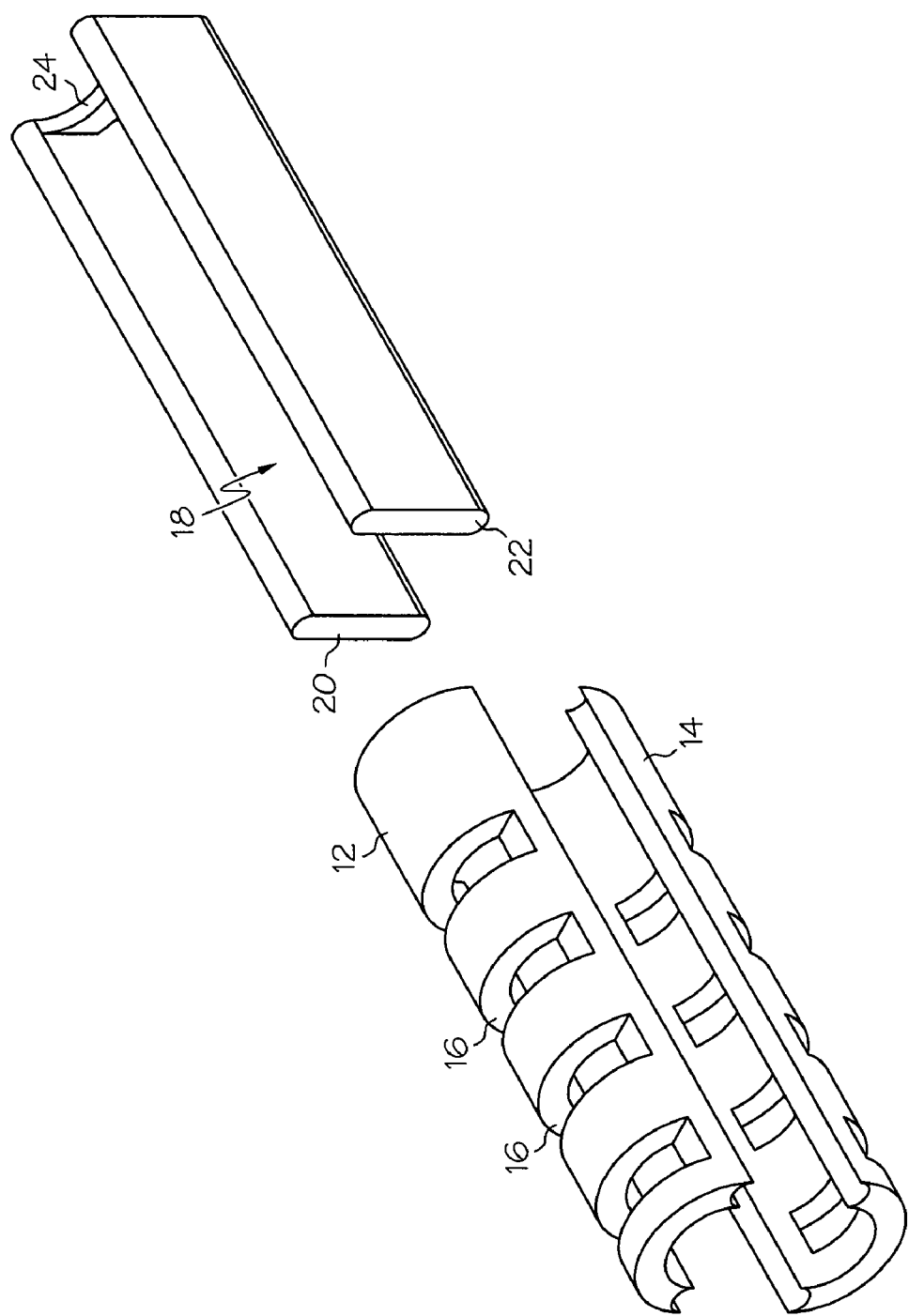
FIG. 2 is an exploded view of a fusion cage constructed in accordance with the teachings of the present invention, showing the aligning portion separate from the two arched portions.

The several embodiments of the fusion cage of the present invention are shown in the figures, wherein like numerals indicate like parts. Turning now to FIG. 1, a fusion cage constructed in accordance with the teachings of the present invention is indicated generally by the numeral 10. Fusion cage 10 of the present invention includes an upper arched housing portion 12 and a lower arched housing portion 14 (hereinafter referred to as upper and lower arched portions). Each of upper and lower arched portions 12 and 14 have a plurality of openings 16 formed therein. Upper arched portion 12 and lower arched portion 14 are connected to one another, and properly aligned, by aligning portion 18. Aligning portion 18 is preferably a single, unitary construction having a first sidewall 20 and a second sidewall 22, the sidewalls being connected by a bridge portion 24 (as shown in FIG. 2). As will become apparent below, aligning portion 18 can be adapted to a variety of sizes, shapes, and forms, thereby determining the overall dimensions of cage 10.

FIG. 2 is an exploded view of a fusion cage 10 constructed in accordance with the teachings of the present invention. In a preferred embodiment, the present device is constructed as shown in FIG. 2, with a single, unitary aligning portion 18 to provide stability to the cage 10. It is contemplated, however, that two separate aligning portions could be used, as will be detailed further below.

Figure 3:
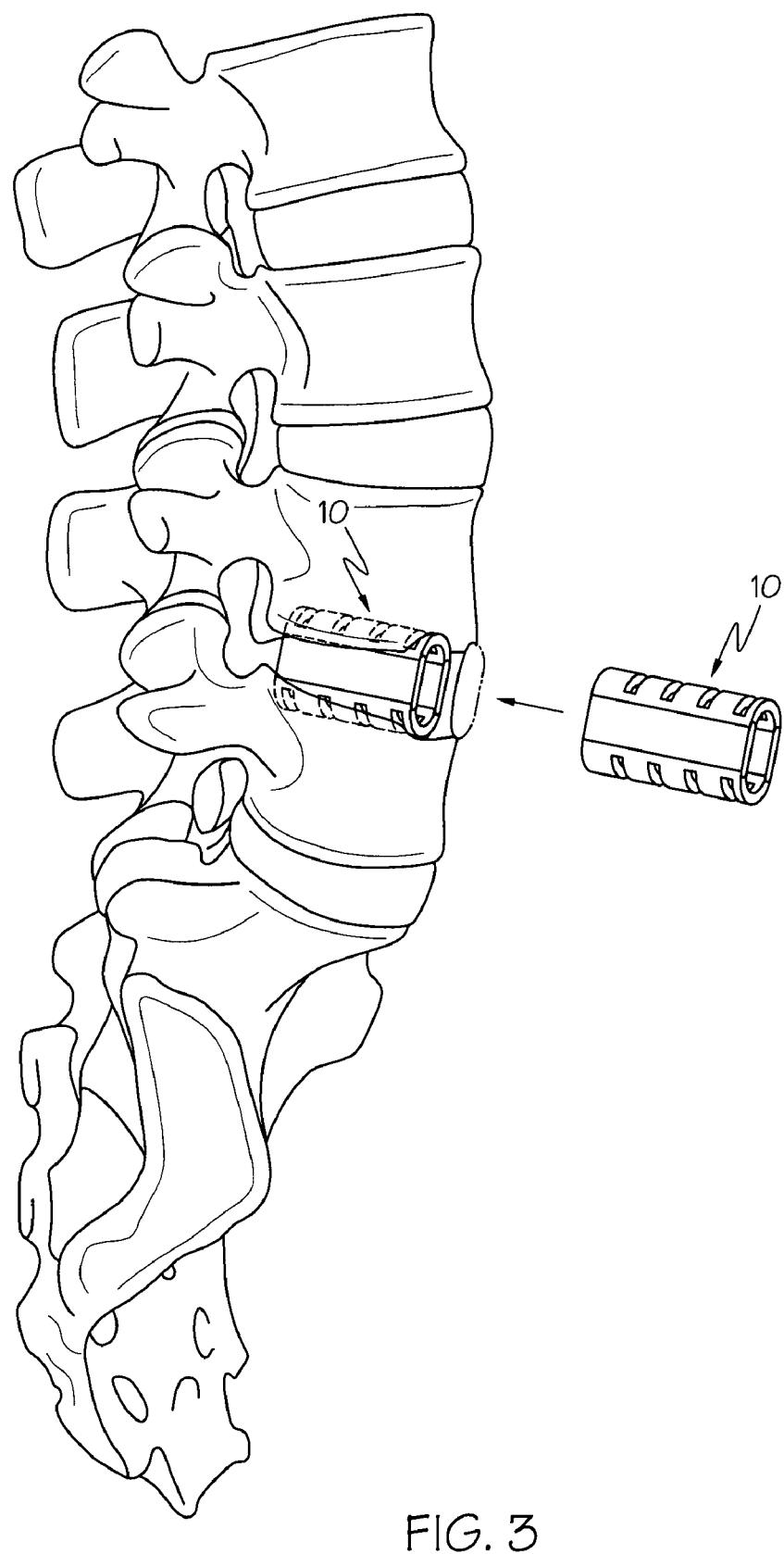
FIG. 3 is a partial cross-sectional side view of one embodiment of the present fusion cage in position in an opening between adjacent vertebrae.

FIG. 3 shows the present device in use, positioned between adjacent vertebrae. In use, arched portions 12 and 14 of the present device are first placed in an opening between two adjacent vertebrae. The opening may be produced by any of a variety of methods known in the art, or by any other suitable means.

Arched portions 12 and 14 are preferably inserted into the opening between adjacent vertebrae by use of distracting forceps, though any other suitable means of inserting the arched members may be used. Once arched portions 12 and 14 are in place, the forceps are opened in order to separate the arched portions to the desired dimensions. While arched portions 12 and 14 are held in place, aligning portion 18 is inserted between them and pushed forward to complete the formation and alignment of cage 10. Other suitable methods of inserting cage 10 may also be used.

Aligning portion 18 is preferably composed of a radiolucent material such as, for example, polyetheretherketone ("PEEK") or carbon fiber. Thus, postoperative radiologic analysis of the fusion contained within cage 10 may be performed. Other suitable materials may also be used, though it is preferred that the material is subject to some sort of postoperative visualization procedure. Examples of suitable radiolucent materials include, but are not limited to, various plastics, such as, for example, nylons, polycarbonates, and polyketones such as polyaryletherketone. Plastics may, if necessary, be reinforced with carbon or glass fibers for use in the present invention.

Although the figures show cage 10 having three openings 26 in each of arched members 12 and 14, it is contemplated that any number of openings of varying size and shape may be used. For example, a single, longitudinal opening could be employed in each of the arched portions and substantially along the length of each of the arched portions. Alternatively, a plurality of fine openings may be provided such at that least a portion of arched portions 12 and 14 is mesh-like in structure. Any configuration of openings may be used so long as such openings are suitable to allow the bone fusion within cage 10 to adhere to the walls of the vertebrae adjacent cage 10. It is preferred that aligning portion 18 is generally rectangular in shape, forming a fusion cage having the shape of a cylinder or trapezoidal cylinder. Other shapes and configurations may also be used.

Figure 4:
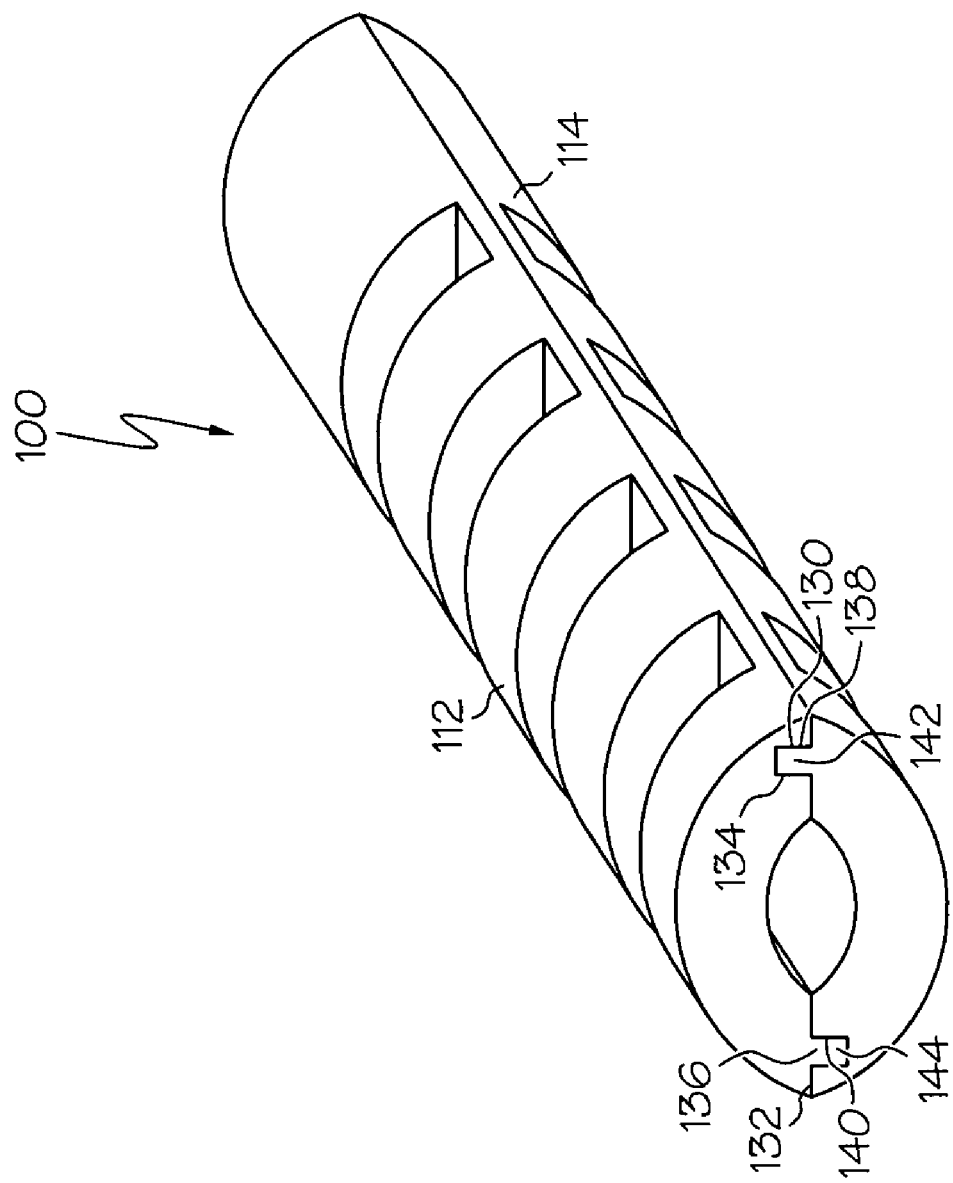
FIG. 4 is a perspective view of an alternative embodiment of the arched portions of a fusion cage, in collapsed form, constructed in accordance with the teachings of the present invention.

FIG. 4 shows an alternative embodiment of a cage 100, in collapsed form, constructed in accordance with the teachings of the present invention. Arched portion 112 includes a first edge 130 and a second edge 132. First edge 130 has a channel 134 running along its longitudinal length, the channel being adapted to receive a corresponding flange such that channel 134 and the corresponding flange mate. Second edge 132 of arched portion 112 has a flange 136 running along its longitudinal length, said flange adapted to be received by a corresponding channel such that flange 136 and the corresponding channel mate. Arched portion 114 also includes a first edge 138 and a second edge 140. First edge 138 of arched portion 114 has a flange 142 running along its longitudinal length, the flange being adapted to be received by a corresponding channel such that flange 142 and the corresponding channel mate. Second edge 140 of arched portion 114 has a channel 144 running along its longitudinal length, the channel being adapted to receive a corresponding flange such that channel 144 and the corresponding flange mate. During the initial insertion of cage 100 into an intervertebral space, arched portion 112 and arched portion 114 will be mated such that channel 134 of arched portion 112 receives flange 142 of arched portion 114, and flange 136 of arched portion 112 is received by channel 144 of arched portion 114.

Figure 5:
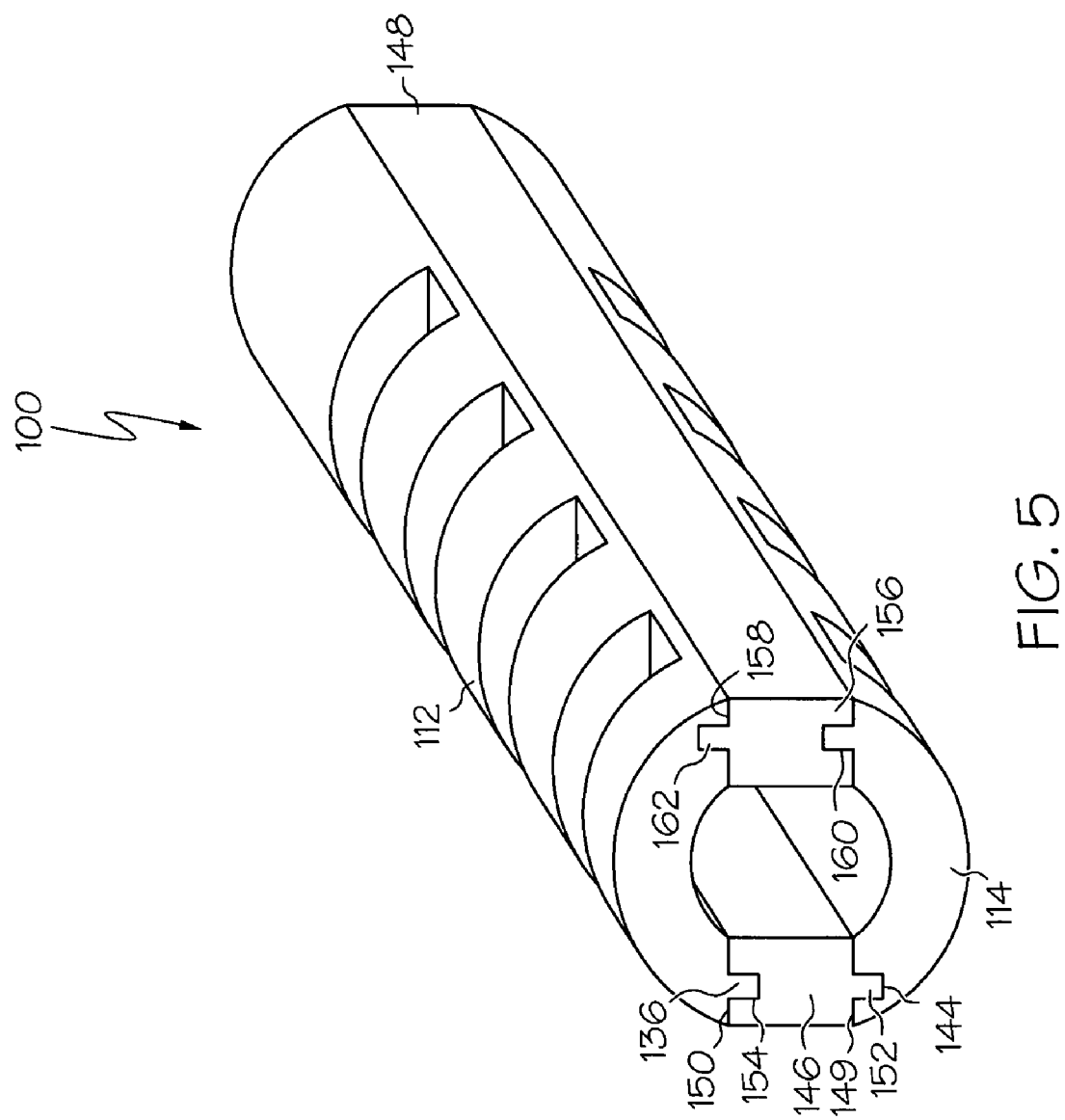
FIG. 5 is a perspective view of an alternative embodiment of a fusion cage constructed in accordance with the teachings of the present invention, shown in complete form with sidewalls inserted therein.

FIG. 5 shows the embodiment of the present invention shown in FIG. 4, with individual aligning sidewalls 146 and 148 included. As is shown in the figure, sidewall 146 has a first edge 149 and a second edge 150. First edge 149 of sidewall 146 has a flange 152 running along the longitudinal length thereof, the flange adapted to be received by channel 144 of arched portion 114. Second edge 150 of sidewall 146 has a channel 154 running along the longitudinal length thereof, the channel adapted to receive flange 136 of arched portion 112. Sidewall 148 has a first edge 156 and a second edge 158. First edge 156 of sidewall 148 has a channel 160 running along the longitudinal length thereof, the channel adapted to receive flange 142 of arched portion 114. Second edge 158 of sidewall 148 has a flange 162 running along the longitudinal length thereof, the flange adapted to be received by channel 134 of arched portion 112. Although the embodiment of the present invention is shown has including channels and flanges for mating of arched portions 112 and 114, or of arched portions 112 and 114 with side walls 146 and 148 to form a complete cage, it is contemplated that other suitable means of mating and aligning the arched portions may also be used.

As shown in the figures, the sidewalls of aligning portion 18, as well as individual aligning sidewalls 146 and 148, are symmetrical, each being of the same height as the other, and each being of a consistent height along its length. In some cases, however, it may be desirable that aligning portions 18 have tapering sidewalls such that cage 10 is wedge-like in overall shape. Such a tapered cage may be useful in addressing problems such as kyphosis or lordosis. Further, sidewalls 20 and 22 of aligning portion 18 may differ in height such that cage 10 is tapered to one side. Alignment portion 18 allows for a good deal of variation in the resultant shape of cage 10, allowing for the treatment of a variety of conditions. Aligning portion 218 may include at least one notch adapted to receive a corresponding nub on one or more of housing portions 212 and 214, such that aligning portion 218 is locked in place and will not slide free of housing portions 212 and 214.

Figure 6:
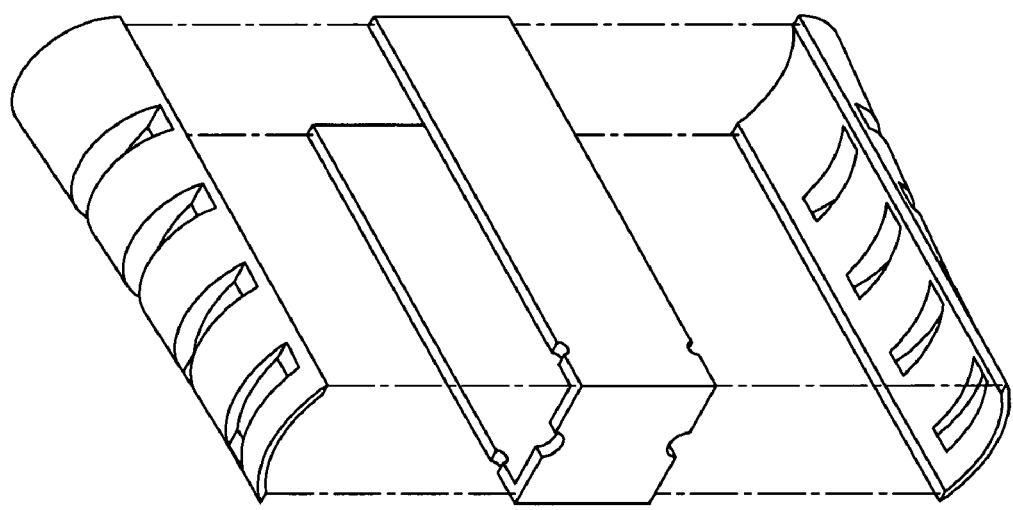
FIG. 6 is an exploded view of one embodiment of the present invention having wedge-shaped housing portions.

FIG. 6 is an exploded view of a preferred embodiment of a fusion cage 200 constructed in accordance with the teachings of the present invention. In a preferred embodiment the present device is constructed with a single, unitary aligning portion to provide stability to the cage. Fusion cage 200 includes a wedge-shaped upper housing portion 212 and a wedge-shaped lower housing portion 214. Wedge-shaped upper housing portion 212 and 214 each have a plurality of openings 216 formed therein. Wedge-shaped upper housing portion 212 and wedge-shaped lower housing portion 214 are connected to one another and properly aligned by aligning portion 218. As noted above, aligning portion 218 is preferably a single, unitary construction having a first sidewall 220 and a second sidewall 222, the sidewalls being connected by a bridge portion 224. Aligning portion 218 also preferably includes a cutout portions 230 for use as described below. As second cutout portion (not shown) is preferably included in an opposing side edge of aligning portion 218 from cutout portion 230.

Figure 7:
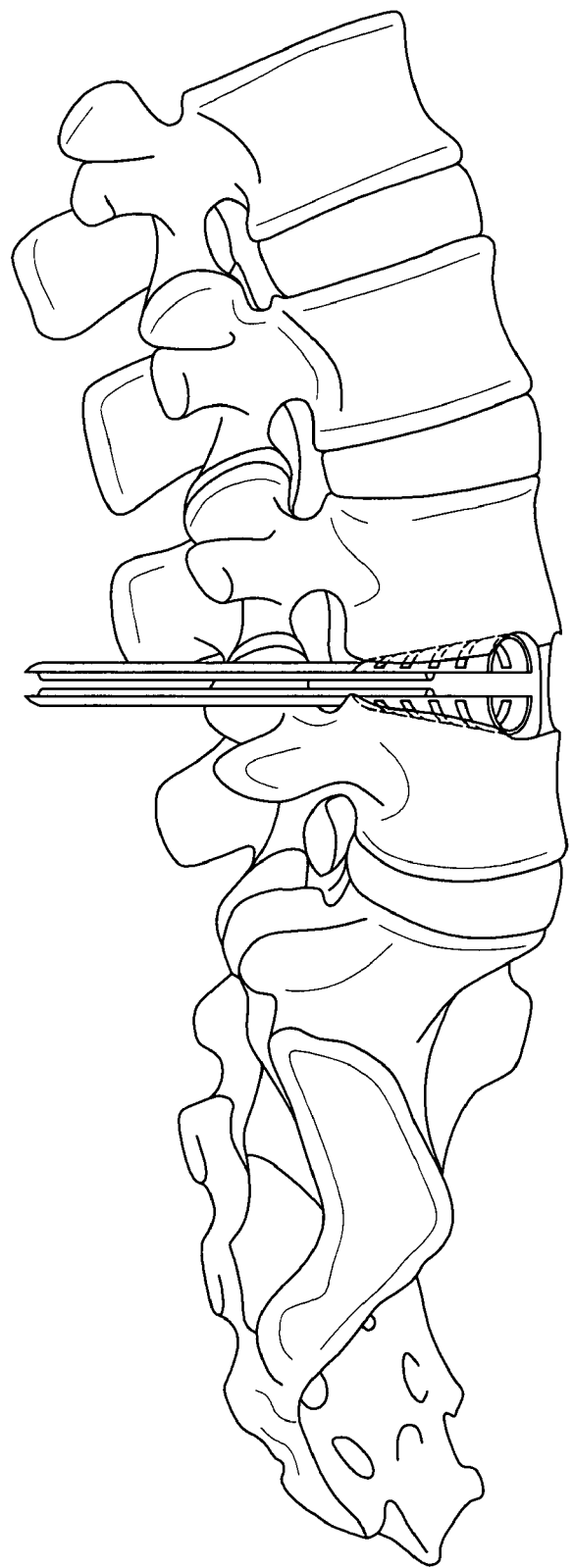
FIG. 7 is a perspective view of one embodiment of the present invention, in collapsed form, inserted between adjacent vertebrae.
Figure 8:
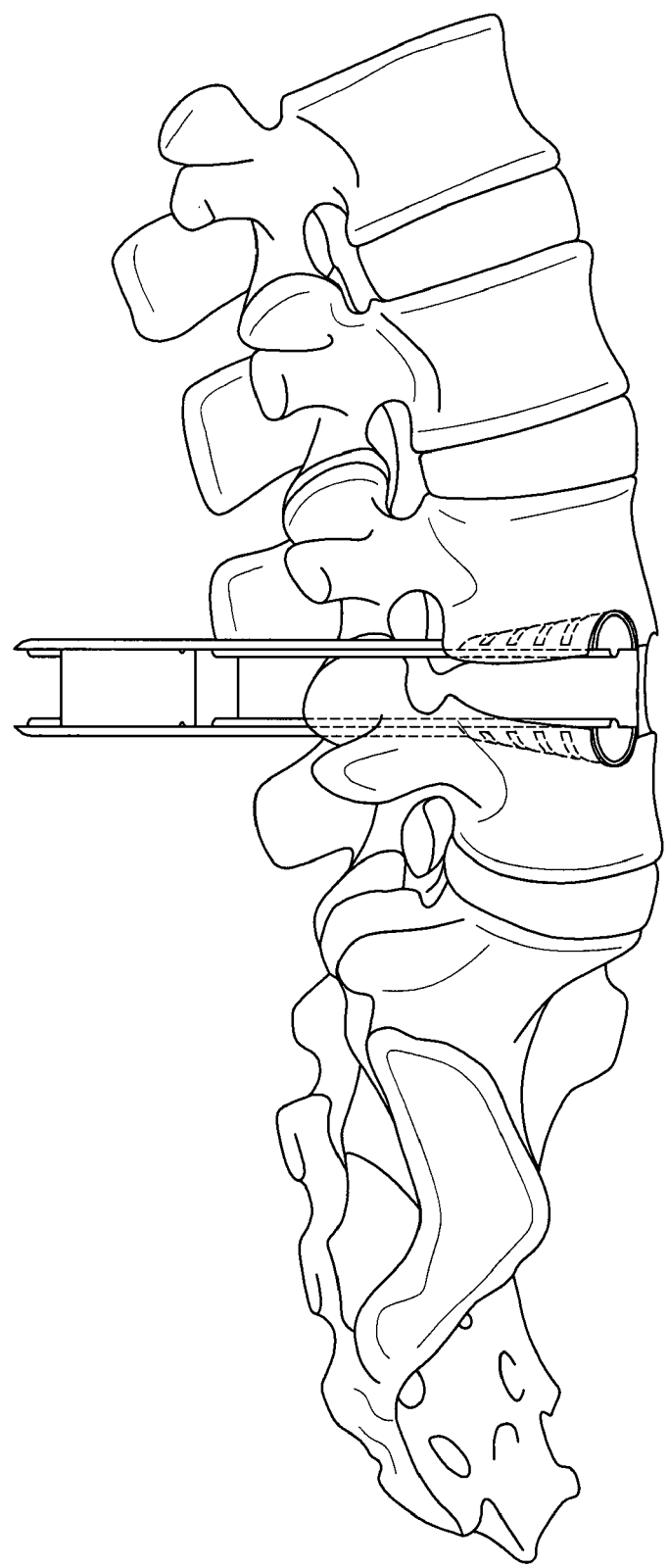
FIG. 8 is a perspective view of one embodiment of the present invention, in expanded form, inserted between adjacent vertebrae.

FIG. 7 shows one embodiment of the housing portions of the present device, in collapsed form, being inserted posteriorly between adjacent vertebrae. Housing portions 212 and 214 are inserted using guide portions 240 and 242. Each of guide portions 240 and 242 have a rail portion, labeled 244 and 246 respectively, associated with an underside thereof. The upper surface of each of said rail portions is preferably sized and shaped so as to be complementary to the interior surface of housing portions 212 and 214, such that guide portions 240 and 242 may be used to stably manipulate housing portions 212 and 214. Rail portions 244 and 246 of guide portions 240 and 242 are preferably sized and shaped such that they mate with cutouts 230 of aligning portion 218, and a cutout (not shown) in an opposing side edge of aligning portion 218 from cutout 230. Thus, once housing portions 212 and 214 are in place, aligning portion 218 can be easily slid into place along rail portions 244 and 246, as shown in FIG. 8. This allows wedge-shaped housing portions 212 and 214 of the present device to be inserted into an opening between vertebrae in collapsed form (thereby allowing entry of the wedged device through openings that would otherwise not allow it to pass). Once the collapsed housing portions are in place, aligning portion 218 is inserted and a completed, wedged fusion cage is in place. Although rail portions 244 and 246 are preferably sized and shaped as indicated above, they may be provided in any suitable size or shape.

Figure 9:
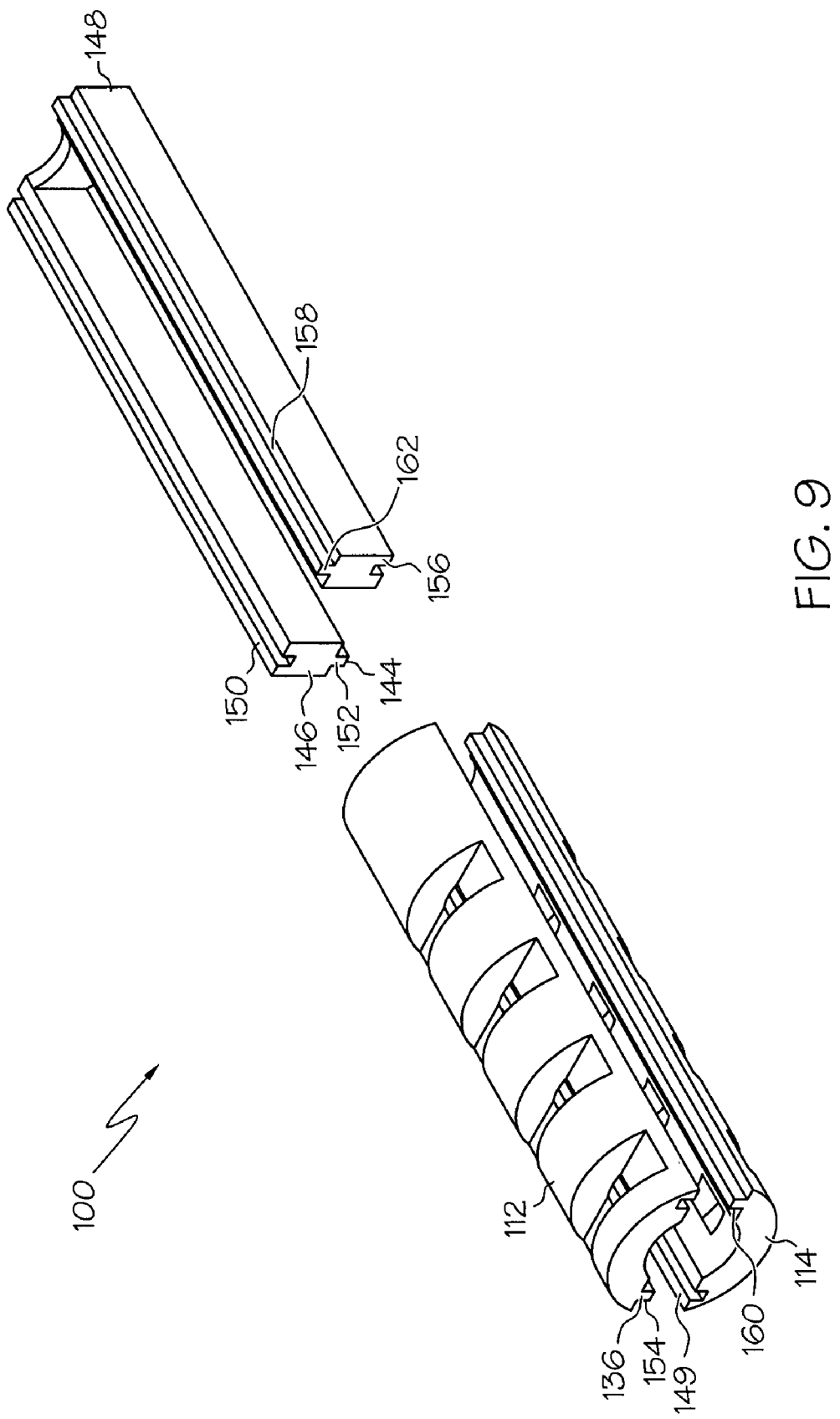
FIG. 9 is a perspective view of one embodiment of the present invention displaying a pair of housing portions and an aligning portion adapted to be received therebetween.
Figure 10:
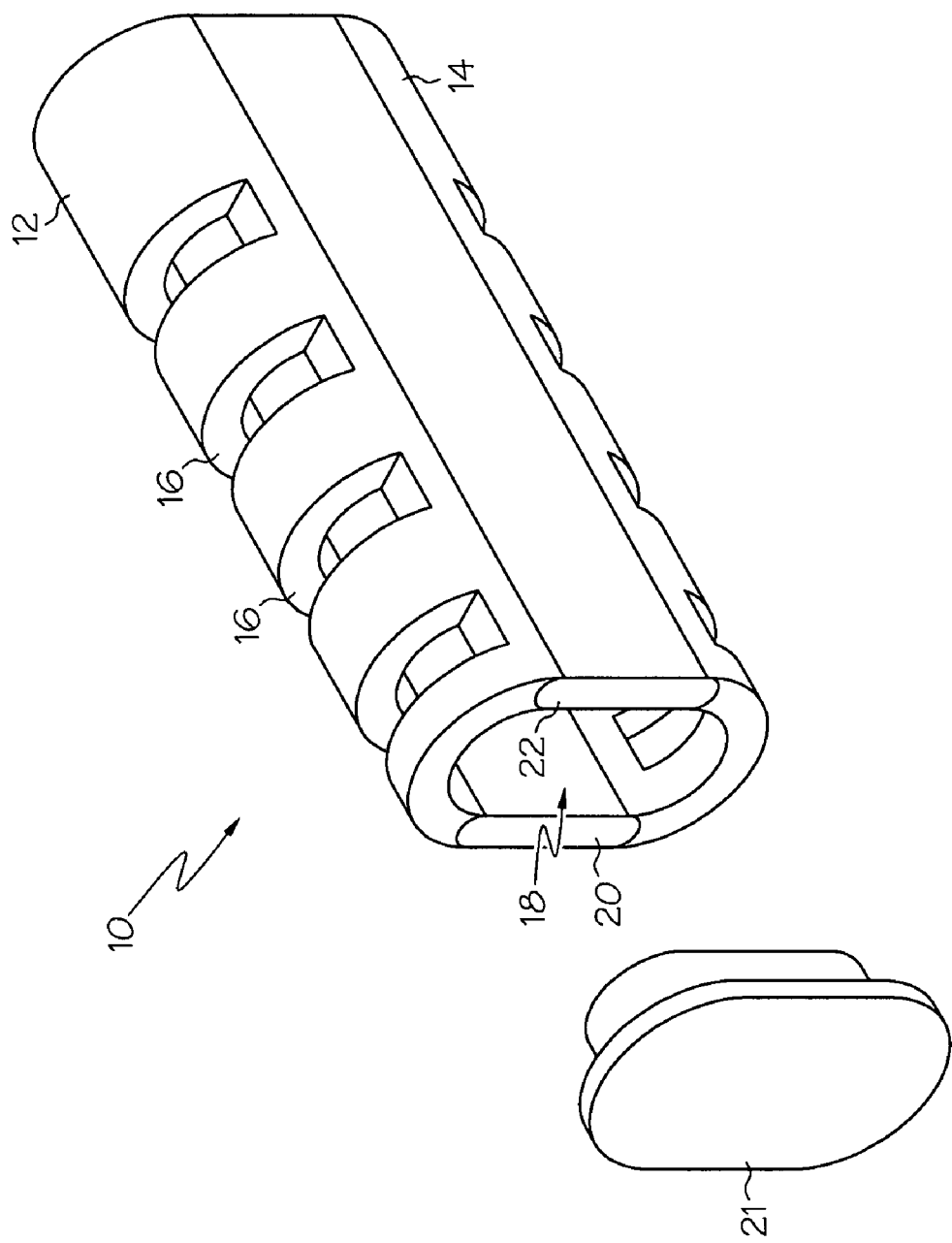
FIG. 10 is a perspective view of one embodiment of the present invention having a cap portion associated therewith.

FIG. 9 provides an alternate view of the embodiment of the present invention shown in FIG. 5. In the view shown in FIG. 9, the alignment portion is shown removed from the housing portions, providing a view of the alignment portion as a single piece with two sidewall portions 146 and 148 joined by a bridge portion similar to bridge portion 24 in FIG. 2. FIG. 10 provides one alternative embodiment of the device shown in FIG. 1, the device in FIG. 10 including an end cap 21 associated therewith.

In any of the embodiments of the present invention, the upper and lower arched portions may be provided with varying wedge configurations, so as to allow a desired degree of lordosis. A preferred desired angle of lordosis is approximately eight degrees, though various other angles may be desired for particular purposes. In embodiments of the present invention using wedge-like arched portions, the arched portions may also be reversed such that a symmetrical cylinder is provided.

In any of the various embodiments of the present invention described above, the arched portions may be provided in a variety of configurations, including waffled, smooth, serrated, saw-toothed, or drilled.

In any of the embodiments of the present invention described above, the fusion cage of the present invention may be packed with bone. In addition, a biologically active compound such as bone morphogenic protein may be included therein. In such embodiments, the present invention preferably includes at least one cap portion that seals an end opening of the fusion cage, thereby containing the bone and/or biologically active material within said fusion cage. Alternatively, a biologically active material may be linked to the interior of the cage via covalent or ionic bonds, or the like, or may be impregnated within the material of the cage itself such that it retains its biological activity.

The foregoing description of the embodiments of the invention has been presented for purposes of illustration and description, and is not intended to be exhaustive or to limit the invention to the precise form disclosed. The description was selected to best explain the principles of the invention and practical application of these principles in order to enable others skilled in the art to best utilize the invention in various embodiments and with such modifications as are suited to the particular use contemplated. It is intended that the scope of the invention not be limited by the specification, but be defined by the claims as set forth below.

The invention claimed is:

1. A fusion cage comprising:
a first housing portion elongated along a longitudinal axis;
a second housing portion elongated along said longitudinal axis; and
an alignment portion including a pair of opposite sidewalls, each of said sidewalls adapted to be received between said first and second housing portions such that said first and second housing portions are held in place by said alignment portion,
wherein said first housing portion includes a first edge and an opposite second edge extending along the length of said first housing portion, and further wherein said second housing portion includes a first edge and an opposite second edge extending along the length of said second housing portion, and further wherein said each of said sidewalls of said alignment portion includes a top edge and an opposite bottom edge, said edges of said first and second housing portion and said edges of said sidewalls including a complementary flange and channel interface for engaging said sidewalls between said housing portions,
wherein said first and second housing portions are arched such that a cylindrical space is defined along said longitudinal axis between said first and second housing portions; and
further wherein said sidewalls of said alignment portion expand said cylindrical space when said alignment portion is received between said first and second housing portions.

2. The fusion cage of claim 1 wherein said first and second housing portions each include a plurality of openings formed therein.

3. The fusion cage of claim 1 wherein said first and second housing portions are constructed from titanium, bone, carbon fiber, polyetheretherketone, and combinations thereof.

4. The fusion cage of claim 1 wherein said alignment portion is constructed from a radiolucent compound.

5. The fusion cage of claim 4 wherein said radiolucent compound is selected from the group consisting of bone, polyetheretherketone, carbon fiber, nylon, polycarbonate, glass, polyketones, polyaryletherketone, and combinations thereof.

* * * * *